(12) United States Patent
Yamazaki et al.

(10) Patent No.: US 8,975,394 B2
(45) Date of Patent: *Mar. 10, 2015

(54) PROCESS FOR PREPARATION OF β-GLYCOSIDE COMPOUNDS

(75) Inventors: Akiko Yamazaki, Funabashi (JP); Yusuke Iriyama, Funabashi (JP); Yoshikazu Ootsuka, Funabashi (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 108 days.

This patent is subject to a terminal disclaimer.

(21) Appl. No.: 13/578,961

(22) PCT Filed: Feb. 7, 2011

(86) PCT No.: PCT/JP2011/052507
§ 371 (c)(1),
(2), (4) Date: Aug. 14, 2012

(87) PCT Pub. No.: WO2011/099442
PCT Pub. Date: Aug. 18, 2011

(65) Prior Publication Data
US 2012/0309958 A1 Dec. 6, 2012

(30) Foreign Application Priority Data

Feb. 15, 2010 (JP) ................. 2010-030149
Dec. 13, 2010 (JP) ................. 2010-277545

(51) Int. Cl.
C08B 37/00 (2006.01)
C07F 7/18 (2006.01)
C07D 405/04 (2006.01)
C07F 7/08 (2006.01)

(52) U.S. Cl.
CPC ............ *C07F 7/1892* (2013.01); *C07D 405/04* (2013.01); *C07F 7/0812* (2013.01)
USPC ........................................................ 536/124

(58) Field of Classification Search
None
See application file for complete search history.

(56) References Cited

U.S. PATENT DOCUMENTS

| 2004/0167096 A1 | 8/2004 | Cheng et al. |
| 2010/0280235 A1 | 11/2010 | Nagai et al. |
| 2011/0054164 A1 | 3/2011 | Sato et al. |

FOREIGN PATENT DOCUMENTS

| FR | 2781229 A1 | 1/2000 |
| JP | 2-152976 A | 6/1990 |
| JP | 5-501404 A | 3/1993 |
| JP | 2003-504377 A | 2/2003 |
| JP | 2006-528972 A | 12/2006 |
| WO | WO 91/06554 A1 | 5/1991 |
| WO | WO 99/29702 A2 | 6/1999 |
| WO | WO 01/04134 A2 | 1/2001 |
| WO | WO 2005/011709 A1 | 2/2005 |
| WO | WO 2009/084655 A1 | 7/2009 |
| WO | WO 2009/125841 A1 | 10/2009 |

OTHER PUBLICATIONS

European Office Action for European Application No. 11742187.5 dated Feb. 10, 2014.
Wuts et al., "Carbonates," Protective Groups in Organic Synthesis, Fourth Edition, 2007, pp. 279-297.
Brakta et al., "Palladium(0)-Based Approach to Functionalized C-Glycopyranosides," J. Org. Chem. (1989), vol. 54, pp. 1890-1896.
Hegedus et al., "Synthesis of 4'-Methyl and 4'-Cyano Carbocyclic 2',3'-Didehydro Nucleoside Analogues via 1,4-Addition to Substituted Cyclopentenones," J. Org. Chem. (2004), vol. 69, pp. 8492-8495.
Hegedus et al., Asymmetric Synthesis of "4'-Elhoxy-2',3'-didehydro-2',3'-dideoxynucleosides by Palladium-Catalyzed Kinetic Discrimination between the Corresponding Disasteroisometric Lactol Acetates," J. Org. Chem (2002), vol. 67, pp. 4076-4080.
Kahn et al., "Pd(0) catalyzed intramolecular alkylation: stereoselective sythesis of furan and isoxazoline-2-oxide analogs." Tetrahedron (2007), vol. 63, pp. 1116-1126.
Saville-Stones et al., "Synthesisof (±)-2',3'-didehydro-2',3'-dideoxy Nucleosides via a Modified Prins Reaction and Palladium (0) Catalysed Coupling," J. Chem. Soc. Perkin Trans 1 (1991), pp. 2603-2604.

(Continued)

*Primary Examiner* — Layla Bland
(74) *Attorney, Agent, or Firm* — Birch, Stewart, Kolasch & Birch, LLP

(57) ABSTRACT

The invention provides a process for producing a β-glycoside compound represented by formula (3), characterized in that the process includes causing to react a cyclic alkene compound represented by formula (1) or (2) with a nucleophile in the presence of a transition metal catalyst.

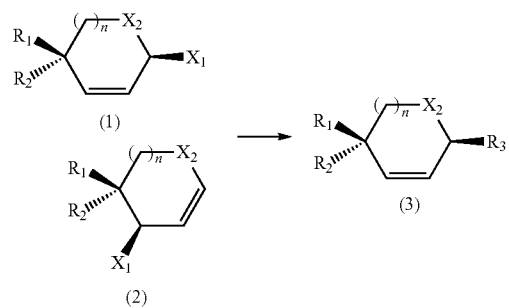

10 Claims, No Drawings

(56) References Cited

OTHER PUBLICATIONS

Bartlett et al., "Exploiting predisposition in the stereoselective synthesis of mono-, bi- and tetracyclic oxygen heterocycles: Equilibration between, and trapping of, alternative di- and tetraacetals," Org. Biomol. Chem., vol. 1, 2003, pp. 2393-2402.

Dupradeau et al., "Differential Solvation and Tautomer Stability of a Model Base Pair within the Minor and Major Grooves of DNA," J. Am. Chem. Soc., vol. 127, 2005, pp. 15612-15617.

International Search Report for International Application No. PCT/JP2011/052508 dated Apr. 26, 2011.

Taverna-Porro et al., "Chemoenzymatic preparation of nucleosides from furanoses," Tetrahedron Letters, vol. 49, 2008, pp. 2642-2645.

Zhou et al., "Synthesis, Structure-Activity Relationships, and Drug Resistance of β-D-3'-Fluoro-2',3'-Unsaturated Nucleosides as Anti-HIV Agents," J. Med. Chem., vol. 47, 2004, pp. 3399-3408.

Chen et al., "Synthesis of 3'-Fluoro-2',3'-dideoxy-2',3'-didehydro-4'-ethynyl-D- and -L-furanosyl Nucleosides," J. Org. Chem., vol. 69, No. 18, 2004, XP008137380, pp. 6034-6041.

Extended European Search Report for European Application No. 11742187.5, dated Jun. 6, 2013.

Hu et al., "One-Pot Synthesis of 5'-Diaryl Esters and Diamidates of Phosphate, Phosphorothioate, and Phosphoroselenoate Derivatives of AZT and d4T," Synthetic Communications: An International Journal for Rapid Communication . . . , vol. 39, No. 8, Mar. 19, 2009, pp. 1342-1354.

Mullah et al., "Potential Prodrug Derivatives of 2',3'-Didehydro-2',3'-dideoxynucleosides, Preparations and Antiviral Activities," J. Med. Chem., vol. 35, 1992, pp. 2728-2735.

Nguyen et al., "Deoxyuridine Triphosphate Nucleotidohydrolase as a Potential Antiparasitic Drug Target," J. Med. Chem., vol. 48, No. 19, 2005, pp. 5942-5954.

Sergheraert et al., "Synthesis and Anti-HIV Evaluation of D4T and D4T 5'-Monophosphate Prodrugs," J. Med. Chem., vol. 36, No. 7, 1993, XP-002311498, pp. 826-830.

Tortolani et al., "Prodrugs of 2',3'-Didehydro-3'-deoxythymidine (D4T): Synthesis, Antiviral Activity, and Rapid Pharmacokinetic Evaluation," Journal of Pharmaceutical Sciences, vol. 83, No. 3, Mar. 1994, pp. 339-343.

Greene et al., Protective Groups in Organic Synthesis, 1999, Third Edition, pp. 17-245.

Houlihan et al., Can. J. Chem., 1985, 63(1), pp. 153-162.

PROCESS FOR PREPARATION OF β-GLYCOSIDE COMPOUNDS

TECHNICAL FIELD

The present invention relates to a novel process for producing β-glycoside compounds.

BACKGROUND ART

Hitherto, there have been known methods for synthesizing β-glycoside compounds from dihydrofuran compounds or the like, and such methods are disclosed in several documents (see, for example, Non-Patent Document 1). In the method disclosed in Document 1, a mixture of an acetylglycoside compound of α-form and the same compound of β-form serving as a raw material is caused to react with a phosphine ligand and a palladium reagent (catalyst), to thereby synthesize a corresponding β-glycoside compound. Document 1 also discloses that an optically active Trost ligand must be used in order to selectively synthesize a β-glycoside compound without forming an α-glycoside compound, and that use of optically inactive diphenylphosphinoferrocene as a ligand results in loss of selectivity, merely yielding a glycoside compound in the α and β mixed form.

In one known case, a specific cyclopentene compound is coupled with ethyl nitroacetate in the presence of tetrakis(triphenylphosphine)palladium. However, α or β selectivity of the product is not disclosed (see, for example, Non-Patent Document 2).

It has been reported that a specific cyclopentene compound (α-form and β-form) serving as a raw material is coupled with imidazole in the presence of tetrakis(triphenylphosphine)palladium, to thereby yield a product (α-form and β-form) with no selectivity (see, for example, Non-Patent Document 3).

Also known is a case in which a specific dihydropyran compound is coupled with a nitromalonic acid ester in the presence of tetrakis(triphenylphosphine)palladium. In this case, reactivity of the α-form raw material is completely the same as that of the β-form raw material (see Non-Patent Document 4).

Yet also known is a case in which a specific cyclopentene compound is coupled with a nucleophile in the presence of tetrakis(triphenylphosphine)palladium. When the nucleophile is adenine, a β-glycoside compound is exceptionally formed. However, when the nucleophile is thymine, no specific selectivity has been reported. Furthermore, it is suggested that, depending on the type of the functional group(s) of the cyclopentene compound, a β-glycoside compound could be selectively yielded only when an optically active Trost ligand is used (see, for example, Non-Patent Document 5).

As described above, those skilled in the art know that difficulty is encountered in selectively yielding a β-glycoside compound through coupling a cyclic alkene compound in the α and β mixed form serving as a raw material in the presence of a transition metal catalyst, unless an expensive optically active ligand is employed.

Meanwhile, β-glycosylation of a compound having a dihydrofuran ring is known to proceed in the presence of a Lewis acid (see, for example, Patent Document 1).

PRIOR ART DOCUMENTS

Patent Documents

Patent Document 1: WO 2009/84655, pamphlet

Non-Patent Documents

Non-Patent Document 1: Journal of Organic Chemistry, Vol. 67, p. 4076 (2002)
Non-Patent Document 2: Tetrahedron, Vol. 63, p. 1116 (2007)
Non-Patent Document 3: Journal of Chemical Society Perkin Transactions 1, p. 2603 (1991)
Non-Patent Document 4: Journal of Organic Chemistry, Vol. 54, p. 1890 (1989)
Non-Patent Document 5: Journal of Organic Chemistry, Vol. 69, p. 8492 (2004)

SUMMARY OF THE INVENTION

Problems to be Solved by the Invention

Thus, an object of the present invention is to provide a process for selectively synthesizing a β-glycoside compound, which process can be performed even by use of an α,β-mixed form cyclic alkene compound, at low cost and on an industrial scale.

Means for Solving the Problems

In order to attain the above object, the present inventors have conducted extensive studies on a novel process for synthesizing a β-glycoside compound.

As a result, through reacting a cyclic alkene compound which can be readily synthesized through various techniques with a nucleophile in the presence of a transition metal catalyst, a β-glycoside compound of interest can be selectively yielded at comparatively high yield. The present invention has been accomplished on the basis of this finding.

Accordingly, the present invention is directed to the following.

[1] A process for producing a β-glycoside compound represented by formula (3):

[F2]

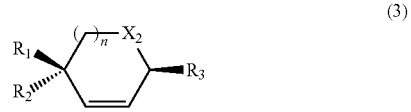

(3)

(wherein $R_1$ represents a halogenated methyl group, an optionally protected formyl group, a C1 to C7 ester group, or an optionally protected hydroxymethylene group; $R_2$ represents an optionally protected hydroxymethylene group, an optionally protected formyl group, a C1 to C7 ester group, a vinyl group, an optionally protected alkynyl group, a cyano group, or an optionally substituted iminomethyl group; $X_2$ represents methylene, an oxygen atom, a sulfur atom, or optionally substituted NH; n is 0 or 1; and $R_3$ represents optionally substituted uracil-1-yl, optionally protected thymin-1-yl, optionally protected thymin-3-yl, optionally amino-protected cytosin-1-yl, imidazol-1-yl, benzimidazol-1-yl, benzo-1,2,3-triazol-1-yl, benzo-1,2,3-triazol-2-yl, optionally substituted thiouracil-1-yl, optionally substituted purin-9-yl, C1 to C7 monoalkylamino, C5 to C21 dialkylamino, C1 to C12 alkoxy, optionally substituted phenoxy, C5 to C21 dialkoxycarbonylmethyl, C5 to C21 diacylmethyl, C1 to C7 acyl(alkoxycarbonyl)methyl, C1 to C7 1-nitroalkyl, C1 to C7 1-cyanoalkyl, or C1 to C7 alkylthio), characterized in that the process comprises causing to react a cyclic alkene compound represented by formula (1) or (2):

[F1]

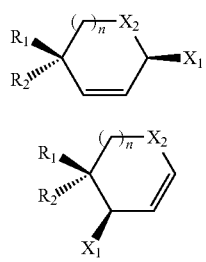

(wherein $R_1$, $R_2$, $X_2$, and n are the same as defined in formula (3), and $X_1$ is an active group) with a nucleophile in the presence of a transition metal catalyst.

[2] A process for producing a β-glycoside compound as recited in [1] above, wherein the nucleophile is $R_3$—H.

[3] A process for producing a β-glycoside compound as recited in [1] above, wherein the nucleophile is thymine.

[4] A process for producing a β-glycoside compound as recited in any of [1] to [3] above, wherein $X_2$ is methylene.

[5] A process for producing a β-glycoside compound as recited in any of [1] to [4] above, wherein $X_1$ is an acetyloxy group.

[6] A process for producing a β-glycoside compound as recited in any of [1] to [5] above, which is performed in the presence of a base.

[7] A process for producing a β-glycoside compound as recited in any of [1] to [6] above, wherein the transition metal catalyst is one or more metallic catalysts selected from among an iron catalyst, a nickel catalyst, a ruthenium catalyst, a rhodium catalyst, a palladium catalyst, an iridium catalyst, a molybdenum catalyst, a tungsten catalyst, and a platinum catalyst.

[8] A process for producing a β-glycoside compound as recited in [7] above, wherein the transition metal catalyst is a palladium catalyst.

[9] A process for producing a β-glycoside compound as recited in any of [1] to [8] above, wherein the transition metal catalyst is a complex catalyst.

[10] A process for producing a β-glycoside compound as recited in any of [1] to [9] above, which further comprises adding a ligand to the process.

Effects of the Invention

According to the present invention, a β-glycoside compound can be produced at high yield under comparatively mild conditions. β-glycoside compounds produced through the production process of the present invention are key intermediate compounds for fine chemicals such as pharmaceuticals, agrochemicals, etc., and use thereof is expected to be expanded.

MODES FOR CARRYING OUT THE INVENTION

Hereinafter, the present invention will be described in detail.

In a preferred embodiment of the present invention, a β-glycoside compound represented by formula (3) is produced in the presence of a transition metal catalyst under basic conditions.

Among the cyclic alkene compounds represented by formula (1) or (2), which are starting substances of the production process of the present invention, a cyclic alkene compound having a dihydrofuran ring may be synthesized from 2-furylmethanol as a starting substance according to a method described in, for example, WO 2009/84655, pamphlet.

Among the cyclic alkene compounds represented by formula (1) or (2), which are starting substances of the production process of the present invention, a cyclic alkene compound having a dihydrothiophene ring may be synthesized from 3-mercaptopropanol as a staring substance according to a method described in, for example, Heterocycles, Vol. 76, p. 1337 (2008).

Among the cyclic alkene compounds represented by formula (1) or (2), which are starting substances of the production process of the present invention, a cyclic alkene compound having a cyclopentene ring may be synthesized from ethyl 2-hydroxyacetate as a starting substance according to a method described in, for example, Bulletin of the Korean Chemical Society, Vol. 29, p. 1723 (2008).

Among the cyclic alkene compounds represented by formula (1) or (2), which are starting substances of the production process of the present invention, a cyclic alkene compound having a dihydropyrrole ring may be synthesized from a diallylamine as a starting substance according to an olefin metathesis method described in, for example, Chemical Communications, Vol. 6, p. 665 (2006).

Among the cyclic alkene compounds represented by formula (1) or (2), which are starting substances of the production process of the present invention, a cyclic alkene compound having a cyclohexene ring may be synthesized from 4-pentyn-1-ol as a starting substance according to a method described in, for example, Tetrahedron Letters, Vol. 50, p. 1279 (2009).

A more specific embodiment of the process of synthesizing the starting substance, which is a cyclic alkene compound having a dihydrofuran ring represented by formula (1) or (2), will now be described. In the synthesis process, the substance of interest may be produced from 2-furylmethanol as a starting material according to, for example, the following reaction scheme. Notably, in the following scheme, N-bromosuccinimide is abbreviated as NBS, tetrahydrofuran as THF, acetic anhydride as $Ac_2O$, Lipase PS Amano SD (trade name, product of Amano Enzyme) as Lipase PS, isopropanol as IPA, trimethylsilyl as TMS, acetonitrile as MeCN, 4-dimethylaminopyridine as DMAP, and ethyl acetate as EtOAc.

[F3]

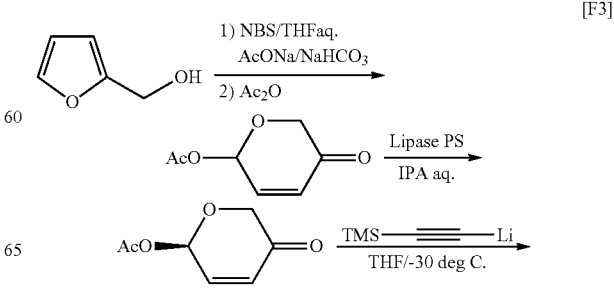

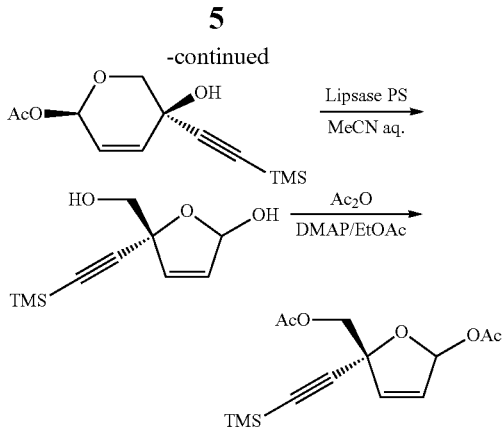

Regarding the stereoisomerism of the cyclic alkene compounds represented by formula (1) or (2) and the β-glycoside compounds represented by formula (3), an isomer having a substituent $X_1$ or $R_3$ on the lower side of the sheet is called an α-form, and another isomer having a substituent $X_1$ or $R_3$ on the upper side of the sheet is called a β-form, when the asymmetric center is fixed on the right side of the ring. Notably, although the compound represented by formula (1) or (2) is a β-form, the same compound of the α-form and β-form (mixture) may also be used in carrying out the present invention.

The present invention will next be described in detail.

In the present invention, the cyclic alkene compound represented by formula (1) or (2) which is an enantiomer mixture may also be used.

Examples of the active group $X_1$ which may be employed in the cyclic alkene compound represented by formula (1) or (2) include an alkylcarbonyloxy group (e.g., acetyloxy), an alkoxycarbonyloxy group (e.g., methoxycarbonyloxy or t-butoxycarbonyloxy), a carbamoyloxy group (e.g., methylaminocarbonyloxy), a phosphoryl group (e.g., dimethylphosphoric acid ester group or diphenylphosphoric acid ester group), and halogen atoms.

These active groups may form a ring structure with a functional group $R_1$ via 1 to 12 atoms (see, for example, the compounds represented by formula (4) or (5)).

[F4]

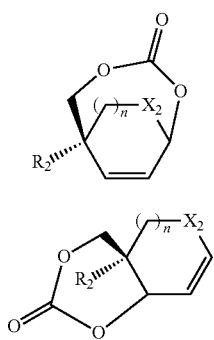

The cyclic alkene compound represented by formula (1) or (2) employed in the present invention may undergo isomerization between α-form and β-form in the reaction system.

The isomerization between α-form and β-form can be accomplished through reaction in the presence of an additive. Examples of the additive include Lewis acids such as alkylated metals (e.g., alkylated zinc and alkylated aluminum), alkoxymetals (e.g., isopropoxytitanium), and metal chlorides (e.g., tin chloride).

The amount of such a Lewis acid added to the reaction system may be 0.001 to 10 eq. (with respect to 1 eq. of reactant), preferably 0.01 to 4 eq.

The reaction of the present invention will next be described in detail.

The metallic catalyst which may be employed in the present invention is preferably a transition metal catalyst, particularly preferably a metallic catalyst selected from among an iron catalyst, a nickel catalyst, a ruthenium catalyst, a rhodium catalyst, a palladium catalyst, an iridium catalyst, a molybdenum catalyst, a tungsten catalyst, and a platinum catalyst.

Examples of the catalyst which may be employed in the reaction are as follows.

Examples of the iron catalyst include iron complex catalysts such as pentacarbonyliron, enneacarbonyldiiron, dodecacarbonyltriirion, dichlorobis(triphenylphosphine)iron, tetracarbonyl(triphenylphosphine)iron, tricarbonylbis(triphenylphosphine)iron, sodium cyclopentadienyldicarbonylferrate, cyclopentadienyldicarbonyliron dimer, pentamethylcyclopentadienyldicarbonyliron dimer, cyclopentadienetricarbonyliron, cyclohexadienetricarbonyliron, butadienetricarbonyliron, sodium tetracarbonylferrate, bis(cyclopentadienyl)iron (ferrocene), bis(tetramethylcyclopentadienyl)iron, bis(methylcyclopentadienyl)iron(1,1'-dimethylferrocene), sodium tricarbonyl(nitroso)ferrate, tetrabutylammonium tricarbonyl(nitrosyl)ferrate, acetylferrocene, and acetylacetonatoiron.

Examples of the nickel catalyst include solid and supported nickel catalysts such as nickel-on-silica, nickel-on-alumina, and nickel-on-carbon; and nickel complex catalysts such as tetracarbonylnickel, dichlorobis(triphenylphosphine)nickel, tetrakis(triphenylphosphine)nickel, tetrakis(triphenylphosphite)nickel, bis(cyclooctadienyl)nickel, and dichloro(diphenylphosphinoethylene)nickel.

Examples of the ruthenium catalyst include supported ruthenium catalysts such as ruthenium-on-silica, ruthenium-on-alumina, and ruthenium-on-carbon; ruthenium complex catalysts such as pentacarbonylruthenium, dodecacarbonyltriruthenium, tetrahydridododecacarbonyltetraruthenium, dihydrido(dinitrogen)tris(triphenylphosphine)ruthenium, dicarbonyltris(triphenylphosphine)ruthenium, tetracarbonyl(trimethylphosphite)ruthenium, pentakis(trimethylphosphite)ruthenium, tris(acetylacetonato)ruthenium, diacetatodicarbonylbis(triphenylphosphine)ruthenium, dichlorobis(chlorotricarbonyl)ruthenium, carbonylchlorohydridotris(triphenylphosphine)ruthenium, tetrahydridotris(triphenylphosphine)ruthenium, acetatohydridotris(triphenylphosphine)ruthenium, dichlorobis(acetonitrile)bis(triphenylphosphine)ruthenium, ruthenocene, bis(pentamethylcyclopentadienyl)ruthenium, dichloro(pentamethylcyclopentadienyl)ruthenium, chloro(cyclopentadienyl)bis(triphenylphosphine)ruthenium, hydrido(cyclopentadienyl)bis(triphenylphosphine)ruthenium, chlorocarbonyl(cyclopentadienyl)ruthenium, hydrido(cyclopentadienyl)(1,5-cyclooctadiene)ruthenium, chloro(cyclopentadienyl)(1,5-cyclooctadiene)ruthenium, dihydridotetrakis(triphenylphosphine)ruthenium, cyclooctatriene(cyclooctadiene)ruthenium, chlorohydridotris(triphenylphosphine)ruthenium, tricarbonylbis(triphenylphosphine)ruthenium, tricarbonyl(cyclooctatetraene)ruthenium, tricarbonyl(1,5-cyclooctadiene)ruthenium, and dichlorotris (triphenylphosphine)ruthenium; and other ruthenium catalysts such as ruthenium chloride, ruthenium oxide, and ruthenium black.

Examples of the palladium catalyst include solid and supported palladium catalysts such as metallic palladium, palladium black, a palladium-on-silica catalyst, a palladium-on-alumina catalyst, a palladium-on-carbon catalyst, a palladium-on-barium sulfate catalyst, a palladium-on-zeolite catalyst, a palladium-on-silica•alumina catalyst, and a palladium-on-polymer catalyst; palladium complex catalysts such as dichlorobis(triphenylphosphine)palladium, dichlorobis(trimethylphosphine)palladium, dichlorobis(tributylphosphine)palladium, bis(tricyclohexylphosphine)palladium, tetrakis(triethylphosphite)palladium, bis(cycloocta-1,5-diene)palladium, tetrakis(triphenylphosphine)palladium, dicarbonylbis(triphenylphosphine)palladium, carbonyltris(triphenylphosphine)palladium, bis[1,2-bis(diphenylphosphino)ethane]palladium, bis[1,4-bis(diphenylphosphino)butane]palladium, dichloro[1,1'-bis(diphenylphosphino)ferrocene]palladium dichlorometnane complex, bis(tri-t-butylphosphine)palladium, bis(tricyclohexylphosphine)palladium, bis(triphenylphosphine)palladium acetate, dichloro[1,2-bis(diphenylphosphino)ethane]palladium, dichlorobis(tri-O-tolylphosphine)palladium, dimethylbis(diphenylmethylphosphine)palladium, dibromobis(tri-t-butylphosphino)dipalladium, tridichlorodiaminepalladium, dichlorobis(acetonitrile)palladium, tetrakis(acetonitrile)palladium tetrafluoroborate, dichlorobis(benzonitrile)palladium, dichloro(1,5-cyclooctadiene)palladium, allylpalladium chloride dimer, bis(2-methylallyl)palladium chloride dimer, bis(dibenzylideneacetone)palladium, tris(dibenzylideneacetone)(chloroform)dipalladium, tris(dibenzylideneacetone)dipalladium, acetylacetonepalladium, 2,4-pentadionepalladium, hexafluoropentadionepalladium, palladium acetate, palladium trifluoroacetate, and palladium trifluoromethanesulfonate; and other palladium catalysts such as palladium chloride and palladium oxide.

Examples of the rhodium catalyst include supported rhodium catalysts such as a rhodium-on-silica catalyst, a rhodium-on-alumina catalyst, and a rhodium-on-carbon catalyst; rhodium complex catalysts such as chlorotris(triphenylphosphine)rhodium, hexadecacarbonylhexarhodium, dodecacarbonyltetrarhodium, dichlorotetracarbonyldirhodium, hydridotetracarbonylrhodium, hydridocarbonyltris(triphenylphosphine)rhodium, hydridotetrakis(triphenylphosphine)rhodium, dichlorobis(cyclooctadiene)dirhodium, dicarbonyl(pentamethylcyclopentadienyl)rhodium, cyclopentadienylbis(triphenylphosphine)rhodium, and dichlorotetrakis(aryl)dirhodium; and other rhodium catalysts such as rhodium chloride and rhodium oxide.

Examples of the iridium catalyst include iridium complex catalysts such as chloro(cyclooctadienyl)iridium dimer.

Examples of the molybdenum catalyst include molybdenum complex catalysts such as hexacarbonylmolybdenum, biscarbonyltetra(isocyano)molybdenum, tricarbonyltris(acetonitrile)molybdenum, pentacarbonylbis(trifluoromethanesulfonyl)molybdenum, dibromotetracarbonylmolybdenum dimer, chlorotetracarbonylbis(acetonitrile)(trichlorostannyl)molybdenum, tetracarbonyl(bipyridyl)molybdenum, tricarbonyl(bipyridyl)(acetonitrile)molybdenum, and (N,N'-bis(cyclohexyl)ethylenediimine)tetracarbonylmolybdenum.

Examples of the tungsten catalyst include tungsten complex catalysts such as tetracarbonyltetra(acetonitrile)tungsten, pentacarbonylbis(trifluoromethanesulfonyl)tungsten, and dibromotetracarbonyltungsten dimer.

Examples of the platinum catalyst include supported platinum catalysts such as a platinum-on-silica catalyst, a platinum-on-alumina catalyst, and a platinum-on-carbon catalyst; platinum complex catalysts such as dichlorobis(triphenylphosphine)platinum, dichlorobis(trimethylphosphine)platinum, dichlorobis(tributylphosphine)platinum, tetrakis(triphenylphosphine)platinum, tetrakis(triphenylphosphite)platinum, tris(triphenylphosphine)platinum, dicarbonylbis(triphenylphosphine)platinum, carbonyltris(triphenylphosphine)platinum, cis-bis(benzonitrile)dichloroplatinum, bis(1,5-cyclooctadiene)platinum, and methylenebis(triphenylphosphine)platinum; and other platinum catalysts such as platinum chloride, platinum oxide (Adams catalyst), and platinum black.

Among these metallic catalysts, a nickel catalyst, a palladium catalyst, a ruthenium catalyst, and a rhodium catalyst are preferred. A complex catalyst is a suitably employed form of the catalyst.

These catalysts may be used singly or in combination.

The amount(s) of transition metal catalyst(s) used in the reaction is generally 0.0001 to 50 mol % with respect to the cyclic alkene compound represented by formula (1) or (2), preferably 0.001 to 20 mol %.

In accordance with needs, a ligand may be added to the aforementioned catalyst. Examples of the ligand include monodentate and polydentate tertiary phosphines such as trimethylphosphine, triethylphosphine, tributylphosphine, triphenylphosphine, tris(p-tolyl)phosphine, tris(2,6-dimethylphenyl)phosphine, sodium diphenylphosphinobenzene-3-sulfonate, bis(3-sulfonatophenyl)phosphinobenzene sodium salt, tri(2-furyl)phosphine, bis(diphenylphosphino)methane, 1,2-bis(diphenylphosphino)ethane, 1,3-bis(diphenylphosphino)propane, 1,4-bis(diphenylphosphino)butane, 2,3-bis(diphenylphosphino)butane, 2,4-bis(diphenylphosphino)pentane, 1,1'-bis(diphenylphosphino)ferrocene, 1,3-bis(diisopropylphosphino)propane, 2,2'-bis(diphenylphosphino)biphenyl, 4,5-bis[(diphenylphosphinyl)methyl]-2,2-dimethyl[1,3]dioxolane, 1,2-bis(O-anisylphenylphosphino)ethane, 2,2'-bis(diphenylphosphino)-1,1'-binaphthyl, Trost ligand, tris(3-sulfonatophenyl)phosphine sodium salt; phosphorous acid esters such as trimethyl phosphite, triethyl phosphite, tripropyl phosphite, tributyl phosphite, triphenyl phosphite, and tris(2,6-dimethylphenyl) phosphite; phosphonium salts such as triphenylmethylphosphonium iodide, triphenylmethylphosphonium bromide, triphenylmethylphosphonium chloride, triphenylallylphosphonium iodide, triphenylallylphosphonium bromide, triphenylallylphosphonium chloride, tetraphenylphosphonium iodide, tetraphenylphosphonium bromide, and tetraphenylphosphonium chloride; phosphoric acid esters such as triphenyl phosphate, trimethyl phosphate, triethyl phosphate, and triallyl phosphate; organic arsines such as triphenylarsine; nitriles such as benzonitrile and acetonitrile; ketones such as acetylacetone; dienes such as cyclopentadiene, pentamethylcyclopentadiene, and 1,5-cyclooctadiene; azo heterocyclic system ligands such as pyridine, 2-picoline, 3-picoline, 4-picoline, 2,2-bipyridyl, terpyridine, 1,10-phenanthroline, 8-hydroxyquinoline, bisoxazolinylpyridine (Pybox), 1,4-dimethylpyrazole, 1,3,5-trimethylpyrazole, pyrimidine, and pyrazine; π acid ligands such as dimethyl maleate, dimethyl fumarate, phenylacetylene, and diphenylacetylene; reaction atmosphere gas such as carbon monoxide; and N-heterocyclic carbenes such as 1,3-bis(2,6-diisopropylphenyl)imidazolium chloride.

When a ligand is added, the amount thereof is generally 0.1 to 10,000 mol % with respect to transition metal catalyst, preferably 1 to 5,000 mol %.

Examples of the base include inorganic bases such as sodium hydroxide, potassium hydroxide, sodium carbonate, potassium carbonate, cesium carbonate, sodium hydrogencarbonate, potassium hydrogencarbonate, and sodium hydride; organic bases such as pyridine, 4-dimethylaminopyridine, triethylamine, tributylamine, N,N-dimethylaniline, and 1,8-diazabicyclo[5.4.0]-7-undecene; organic lithiums such as butyllithium and s-butyllithium; organic lithiumamides such as lithiumdiisopropylamide and lithiumbis(trimethylsilyl)amide; and metal alkoxides such as sodium methoxide, sodium ethoxide, and potassium t-butoxide. Among them, bases such as sodium carbonate, potassium carbonate, sodium hydrogencarbonate, triethylamine, and sodium hydride are preferred, with sodium hydride being more preferred.

The base is generally used in an amount of 0 to 10 eq. with respect to 1 eq. of the reactant compound, preferably 0 to 2 eq.

Examples of the nucleophile represented by $R_3$—H which may be employed in the reaction include heterocyclic bases (such as optionally substituted uracils, optionally protected thymines (e.g., 4-O-methylthymine), cytosine, imidazole, benzimidazole, benzotriazole, optionally substituted thiouracils, and purines), monoalkylamines, dialkylamines, alcohols, optionally substituted phenols, malonic acid esters, acetylacetones, acetoacetic acid esters, nitromethylene compounds, cyanomethylene compounds, and thiols. Examples of preferred nucleophiles include optionally substituted uracils, optionally protected thymines, cytosine, imidazole, benzimidazole, benzotriazole, optionally substituted thiouracils, optionally substituted purines, C1 to C7 monoalkylamines, C2 to C14 dialkylamines, C1 to C12 alcohols, optionally substituted phenols, C5 to C20 malonic acid esters, acetylacetone, C5 to C20 acetoacetic acid esters, C1 to C7 nitromethylene compounds, C1 to C7 cyanomethylene compounds, and C1 to C7 thiols. Through increasing the nucleophile amount, a β-glycoside compound can be produced at higher yield.

Examples of the group $R_3$ include optionally substituted uracil-1-yl, optionally protected thymin-1-yl, optionally protected thymin-3-yl, optionally amino-protected cytosin-1-yl, imidazol-1-yl, benzimidazol-1-yl, benzo-1,2,3-triazol-1-yl, benzo-1,2,3-triazol-2-yl, optionally substituted thiouracil-1-yl, optionally substituted purin-9-yl, C1 to C7 monoalkylamino, C5 to C21 dialkylamino, C1 to C12 alkoxy, optionally substituted phenoxy, C5 to C21 dialkoxycarbonylmethyl, C5 to C21 diacylmethyl, C1 to C7 acyl(alkoxycarbonyl)methyl, C1 to C7 1-nitroalkyl, C1 to C7 1-cyanoalkyl, and C1 to C7 alkylthio.

As used herein, the expression "optionally substituted" refers to that a hydrogen atom or hydrogen atoms are optionally substituted by one or more substituents, which are identical to or different from one another, selected from among a halogen atom, a C1 to C7 alkyl group, a C1 to C7 alkoxy group, a C6 to C12 aryl group, a carboxyl group, a C1 to C7 acyl group, a nitro group, and a cyano group.

Also, as used herein, the expression "optionally protected" refers to that a group is optionally protected by a protective group which is employed in general organic synthetic reaction.

Protective groups preferably in the reaction are as follows.

Examples of the protective group for a hydroxy group or a mercapto group include alkyl protective groups such as methyl, benzyl, p-methoxybenzyl, and t-butyl; acetal protective groups such as methoxymethyl, 2-tetrahydropyranyl, and ethoxyethyl; acyl protective groups such as acetyl, pivaloyl, and benzoyl; and silyl protective groups such as trimethylsilyl, triethylsilyl, t-butyldimethylsilyl, triisopropylsilyl, and t-butyldiphenylsilyl.

Examples of the amino-group-protective group include protective groups forming carbamate such as t-butoxycarbonyl, benzyloxycarbonyl, 9-fluorenylmethyloxycarbonyl, 2,2,2-trichloroethoxycarbonyl, and allyloxycarbonyl; protective groups forming amide such as trifluoroacetyl; protective groups forming imide such as phthaloyl; and protective groups forming sulfonamide such as p-toluenesulfonyl or 2-nitrobenzenesulfonyl.

Examples of the ketone-protective group include protective groups forming cyclic or acyclic acetal such as dimethylacetal, ethylene glycol acetal, 1,3-propanediol acetal, or dithioacetal.

Examples of the carboxyl-group-protective group include protective groups forming ester such as a methyl ester, an ethyl ester, a benzyl ester, or a t-butyl ester.

Examples of the alkynyl-group-protective group include silyl protective groups such as trimethylsilyl, triethylsilyl, t-butyldimethylsilyl, triisopropylsilyl, and t-butyldiphenylsilyl.

In order to attain smooth reaction, the nucleophile may be siliyalted in advance with a silylating reagent such as chlorotrimethylsilane or bistrimethylsilylacetamide.

Preferably, the reaction is performed under solvent-diluted conditions for smoothly performing the reaction including sufficient mixing and dispersing the reagents used in the reaction. No particular limitation is imposed on the solvent employed in the reaction, so long as the solvent is inert to the reaction. Examples of the solvent include ethers such as diethyl ether, methyl t-butyl ether, tetrahydrofuran, diethyl ether, dimethoxymethane, diethoxymethane, ethylene glycol dimethyl ether, ethylene glycol diethyl ether, ethylene glycol dibutyl ether, diethylene glycol dimethyl ether, diethylene glycol diethyl ether, diethylene glycol dibutyl ether, triethylene glycol dimethyl ether, 1,4-dioxane, and anisole; alcohols such as methanol, ethanol, 1-propanol, 2-propanol, 1-butanol, 2-butanol, isobutanol, 2-methyl-2-propanol, methyl cellosolve, ethyl cellosolve, i-propyl cellosolve, diethylene glycol monomethyl ether, diethylene glycol monoethyl ether, diethylene glycol monobutyl ether, cyclohexanol, and benzyl alcohol; ketones such as acetone, methyl ethyl ketone, diethyl ketone, 2-pentanone, methyl isobutyl ketone, and cyclohexanone; aliphatic hydrocarbons such as pentane, hexane, cyclohexane, methylcyclohexane, heptane, octane, and decane; halohydrocarbons such as chloroform, tetrachlorocarbon, dichloroethane, and tetrachloroethylene; aromatic hydrocarbons such as benzene, toluene, xylene, chlorobenzene, o-dichlorobenzene, m-dichlorobenzene, p-dichlorobenzene, nitrobenzene, and tetrahydronaphthalene; nitriles such as acetonitrile and propionitrile; esters such as methyl acetate, ethyl acetate, butyl acetate, and ethyl propionate; amides such as N,N-dimethylformamide, N,N-dimethylacetamide, and N-methylpyrrolidone; ureas such as 1,3-dimethylimidazolidinone and N,N,N',N'-tetramethylurea; pyridines such as pyridine, 2-picoline, 3 picoline, 4-picoline, and 5-ethyl-2-picoline; and water. These solvents may be used singly or in combination.

The reaction may be carried out in a wide temperature range. However, when economic factors including the amount(s) of reagent(s) used in the reaction are taken into consideration, generally, the reaction temperature is preferably −80 to 100° C., particularly preferably −20 to 50° C. Alternatively, the reaction may be performed at room temperature.

The reaction time (i.e., the time required for terminating the reaction), which varies depending on the amount of reactant used in the reaction, reactant concentration, reaction temperature, etc., is generally 0.1 to 20 hours, preferably 0.5 to 10 hours.

The reaction may be carried out in a batch manner or in a continuous manner. The reaction format may be chosen depending on the substrate concentration, percent conversion, productivity, etc. required for the reaction.

After completion of reaction, the solvent remaining in the reaction system is evaporated in accordance with needs, and the reaction mixture is distilled, to thereby directly yield a target product. Alternatively, the crude reaction product is sufficiently washed with water and a solvent which is not dissolved in water, and the obtained organic layer is subjected to a routine work-up process such as distillation or column chromatography, to thereby purify and isolate a β-glycoside compound.

EXAMPLES

The present invention will next be described in more detail by way of examples, which should not be construed as limiting the invention thereto.

$^1$H-NMR and LC were measured by means of the following apparatuses under the following conditions (NMR: nuclear magnetic resonance spectrometry, LC: liquid chromatography).

$^1$H-NMR
Apparatus: JNM-ECP300 (product of JEOL) (300 MHz)
Solvent: CDCl$_3$
[2] LC
LC measurement conditions 1: Analysis of β/α ratio of 2-acetyloxy-5-acetyloxymethyl-5-(2-trimethylsilylethynyl)-2,5-dihydrofuran
    LC: Agilent 1100
    Column: Capcellpak C18 MGII 4.6×100 mm 3 μm
    Oven Temp: 40° C.
    Eluent: CH$_3$CN, H$_2$O
    CH$_3$CN=20% (0 min)→80% (15 min)→80% (17 min)
    Flow rate: 1.2 mL/min
    Detector: UV 195 nm
LC measurement conditions 2: Analysis of β/α ratio of 5-acetyloxymethyl-5-(2-trimethylsilylethynyl)-2-(thymin-1-yl)-2,5-dihydrofuran
    LC: Agilent 1100
    Column: Inertsil Ph-3 4.0×150 mm 3 μm
    Oven Temp: 40° C.
    Eluent: CH$_3$CN/H$_2$O=3/5
    Flow rate: 1.0 mL/min
    Detector: UV 254 nm Example 1

Production of β-5-acetyloxymethyl-5-(2-trimethylsilylethynyl)-2-(thymin-1-yl)-2,5-dihydrofuran represented by formula (A)

[F5]

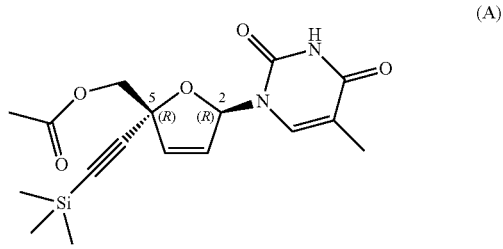

(A)

2-Acetyloxy-5-acetyloxymethyl-5-(2-trimethylsilylethynyl)-2,5-dihydrofuran (β form/α form=81/19), synthesized according to the method disclosed in WO 2009/84655 (pamphlet) (25 mg), and thymine (53 mg) were dissolved in N,N'-dimethylformamide (5 mL). To the solution, tetrakis(triphenylphosphine)palladium(0) (9.7 mg) and sodium hydride (purity: 50%) (4.0 mg) were added, and the reaction was stirred at room temperature for 6 minutes. The reaction mixture was quenched by adding 5% aqueous acetic acid (1 mL) thereto. The yield of β-5-acetyloxymethyl-5-(2-trimethylsilylethynyl)-2-(thymin-1-yl)-2,5-dihydrofuran was calculated through quantitative analysis, and stereochemistry (β/α ratio) was determined from the HPLC peak area ratio (yield: 57%, β/α=97/3).

Example 2

Production of β-5-acetyloxymethyl-5-(2-trimethylsilylethynyl)-2-(thymin-1-yl)-2,5-dihydrofuran represented by formula (A)

2-Acetyloxy-5-acetyloxymethyl-5-(2-trimethylsilylethynyl)-2,5-dihydrofuran (β form/α form=81/19) synthesized according to the method disclosed in WO 2009/84655 (pamphlet) (25 mg), and thymine (21 mg) were dissolved in N,N'-dimethylformamide (5 mL). To the solution, tetrakis(triphenylphosphine)palladium(0) (9.7 mg) and sodium hydride (purity: 50%) (4.0 mg) were added, and the mixture was stirred at room temperature for 10 minutes. The reaction mixture was quenched by adding 5% aqueous acetic acid (1 mL) thereto. The yield of β-5-acetyloxymethyl-5-(2-trimethylsilylethynyl)-2-(thymin-1-yl)-2,5-dihydrofuran was calculated through quantitative analysis, and stereochemistry (β/α ratio) was determined from the HPLC peak area ratio (yield: 47%, β/α=95/5).

The $^1$H-NMR measurements of the compounds formed in Examples 1 and 2 are as follows.

$^1$H-NMR: δ H (300 MHz; CDCl$_3$) 8.09 (brs, 1.00H), 7.24 (d, 1.00H, J=1.0), 7.10 (dd, 1.00H, J=2.0, 1.5), 6.21 (dd, 1.00H, J=4.0, 2.0), 5.93 (dd, 1.00H, J=4.0, 2.0), 4.57 (d, 1.00H, J=12.0), 4.22 (d, 1.00H, J=12.0), 2.10 (s, 3.00H), 1.92 (s, 3.00H), 0.18 (s, 9.00H).

INDUSTRIAL APPLICABILITY

According to the process of the present invention, a β-glycoside compound can be produced at high yield under comparatively mild conditions. β-glycoside compounds produced through the production process of the present invention are key intermediate compounds for fine chemicals such as pharmaceuticals, agrochemicals, etc., and use thereof is expected to be expanded.

The invention claimed is:
1. A process for producing a β-glycoside compound represented by formula (3):

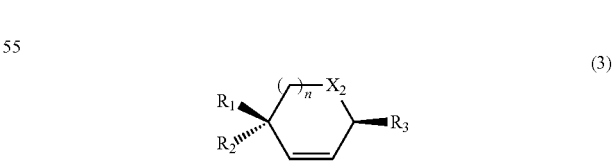

(3)

wherein R$_1$ represents a halogenated methyl group, an optionally protected formyl group, a C1 to C7 ester group, or an optionally protected hydroxymethylene group; R$_2$ represents an optionally protected hydroxymethylene group, an optionally protected formyl group, a C1 to C7 ester group, a vinyl group, an optionally protected alkynyl group, a cyano group, or an optionally substituted iminomethyl group; X$_2$ represents an oxygen atom; n is 0 or 1; and $R_3$ represents optionally substituted uracil-1-yl, optionally protected thymin-1-yl, optionally protected thymin-3-yl, optionally amino-protected cytosin-1-yl, imidazol-1-yl, benzimidazol-1-yl, benzo-1,2,3-triazol-1-yl, benzo-1,2,3-triazol-2-yl, optionally substituted thiouracil-1-yl, optionally substituted purin-9-yl, C1 to C7 monoalkylamino, C5 to C21 dialkylamino, C1 to C12 alkoxy, optionally substituted phenoxy, C5 to C21 dialkoxycarbonylmethyl, C5 to C21 diacylmethyl, C1 to C7 acyl(alkoxycarbonyl)methyl, C1 to C7 1-nitroalkyl, C1 to C7 1-cyanoalkyl, or C1 to C7 alkylthio, characterized in that the process comprises causing to react, with a nucleophile in the presence of a transition metal catalyst and a base different from the nucleophile, a glycoside compound represented by formula (1) or formula (2) or formula (4) or formula (5):

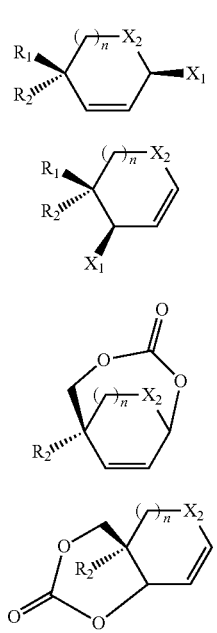

wherein $R_1$, $R_2$, $X_2$, and n are the same as defined in formula (3), and $X_1$ is an active group selected from the group consisting of alkylcarbonyloxy groups, alkoxycarbonyloxy groups, carbamoyloxy groups, phosphoryl groups, and halogen atoms.

2. A process for producing a β-glycoside compound according to claim 1, wherein the nucleophile is $R_3$—H.

3. A process for producing a β-glycoside compound according to claim 1, wherein the nucleophile is thymine.

4. A process for producing a β-glycoside compound according to claim 1, wherein $X_1$ is an acetyloxy group.

5. A process for producing a β-glycoside compound according to claim 1, wherein the transition metal catalyst is one or more metallic catalysts selected from among an iron catalyst, a nickel catalyst, a ruthenium catalyst, a rhodium catalyst, a palladium catalyst, an iridium catalyst, a molybdenum catalyst, a tungsten catalyst, and a platinum catalyst.

6. A process for producing a β-glycoside compound according to claim 5, wherein the transition metal catalyst is a palladium catalyst.

7. A process for producing a β-glycoside compound according to claim 1, wherein the transition metal catalyst is a complex catalyst.

8. A process for producing a β-glycoside compound according to claim 1, which further comprises adding a ligand to the process.

9. A process for producing a β-glycoside compound according to claim 1, wherein the base is sodium hydride.

10. A process for producing a β-glycoside compound according to claim 1, wherein $R_2$ represents an optionally protected alkynyl group.

* * * * *